(12) United States Patent
Zhu et al.

(10) Patent No.: US 10,981,983 B2
(45) Date of Patent: Apr. 20, 2021

(54) ANTIBODY TARGETING INTERLEUKIN 17A AND PREPARATION METHOD AND APPLICATION THEREOF

(71) Applicant: Huabo Biopharm (Shanghai) Co., Ltd., Shanghai (CN)

(72) Inventors: Xiangyang Zhu, Shanghai (CN); Mingqing Cai, Shanghai (CN); Haijia Yu, Shanghai (CN); Huifeng Jia, Shanghai (CN); Ling Yu, Shanghai (CN)

(73) Assignee: Huabo Biopharm (Shanghai) Co., Ltd., Shanghai (CN)

( * ) Notice: Subject to any disclaimer, the term of this patent is extended or adjusted under 35 U.S.C. 154(b) by 61 days.

(21) Appl. No.: 16/461,128

(22) PCT Filed: Jan. 19, 2018

(86) PCT No.: PCT/CN2018/073458
§ 371 (c)(1),
(2) Date: May 15, 2019

(87) PCT Pub. No.: WO2019/015282
PCT Pub. Date: Jan. 24, 2019

(65) Prior Publication Data
US 2020/0071394 A1 Mar. 5, 2020

(30) Foreign Application Priority Data
Jul. 21, 2017 (CN) .......................... 201710602383.3

(51) Int. Cl.
*C07K 16/24* (2006.01)
*C07K 14/725* (2006.01)
*C07K 14/54* (2006.01)
*A61K 39/00* (2006.01)

(52) U.S. Cl.
CPC ........ *C07K 16/244* (2013.01); *C07K 14/7051* (2013.01); *A61K 2039/505* (2013.01); *C07K 2317/24* (2013.01); *C07K 2317/565* (2013.01); *C07K 2317/622* (2013.01); *C07K 2317/92* (2013.01); *C07K 2319/01* (2013.01)

(58) Field of Classification Search
None
See application file for complete search history.

(56) References Cited

U.S. PATENT DOCUMENTS

| | | | |
|---|---|---|---|
| 8,669,345 B2 | 3/2014 | Lee et al. | |
| 9,193,788 B2 | 11/2015 | De Padova et al. | |
| 9,228,015 B2 | 1/2016 | Lee et al. | |
| 9,862,765 B2 | 1/2018 | Zhang et al. | |
| 10,017,568 B2 | 7/2018 | Rommelaere et al. | |
| 2011/0236390 A1 | 9/2011 | Almagro et al. | |
| 2017/0081401 A1 | 3/2017 | Ulitin et al. | |

FOREIGN PATENT DOCUMENTS

| | | |
|---|---|---|
| CN | 103215293 A | 7/2013 |
| CN | 103717618 A | 4/2014 |
| CN | 104936981 A | 9/2015 |
| CN | 105073775 A | 11/2015 |
| CN | 106336459 A | 1/2017 |
| CN | 106795219 A | 5/2017 |
| JP | 2013-509193 A | 3/2013 |

OTHER PUBLICATIONS

International Search Report in PCT Appln. PCT/CN2018/073458 dated Apr. 19, 2018; 8 pages.

*Primary Examiner* — Bridget E Bunner
*Assistant Examiner* — Fozia Hamud
(74) *Attorney, Agent, or Firm* — Kilpatrick Townsend and Stockton LLP

(57) ABSTRACT

The present invention provides an antibody targeted to interleukin 17A (IL-17A), preparation method and the use thereof. In particular, the invention provides a novel anti-IL-17A monoclonal antibody. The antibody of the present invention is capable of binding IL-17A antigen with high specificity, has high affinity and low immunogenicity, and is used for preparing a medicament for preventing or treating an IL-17A-related disease such as various inflammatory or autoimmune diseases.

16 Claims, 1 Drawing Sheet
Specification includes a Sequence Listing.

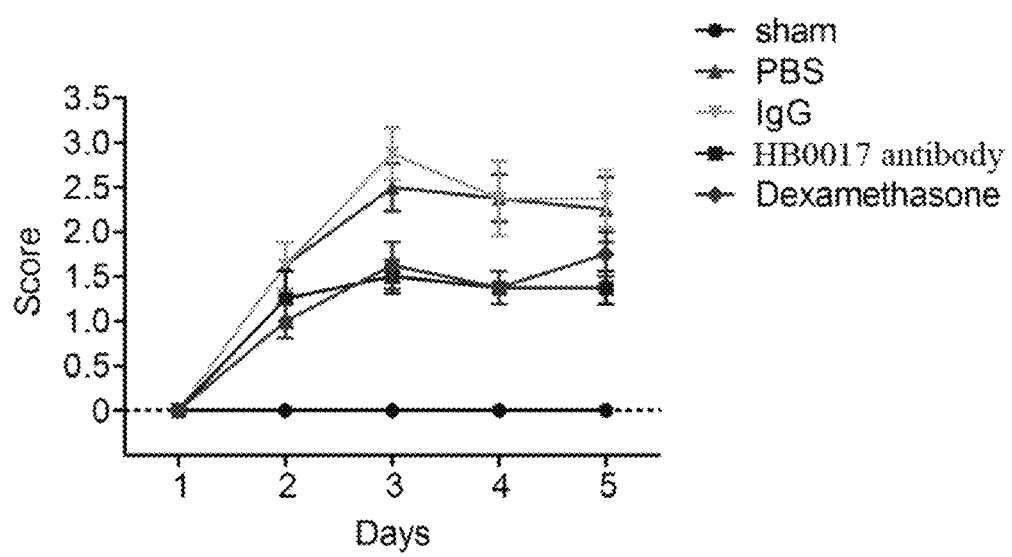

SEQUENCE LISTING

```
<160> NUMBER OF SEQ ID NOS: 11

<210> SEQ ID NO 1
<211> LENGTH: 117
<212> TYPE: PRT
<213> ORGANISM: Mus musculus

<400> SEQUENCE: 1

Gln Ile Gln Leu Val Gln Ser Gly Pro Glu Leu Lys Lys Pro Gly Glu
1               5                   10                  15

Thr Val Lys Ile Ser Cys Lys Ala Ser Glu Tyr Ile Phe Thr Asn Tyr
            20                  25                  30

Gly Met Asn Trp Val Lys Glu Ala Pro Gly Lys Ala Phe Lys Trp Met
        35                  40                  45

Gly Trp Ile Asp Thr Asn Thr Gly Glu Pro Thr Tyr Ala Glu Asp Phe
    50                  55                  60

Lys Gly Arg Phe Ala Phe Ser Leu Asp Ser Ser Ala Thr Ser Ala Phe
65                  70                  75                  80

Leu Gln Ile Ser Asn Leu Lys Asp Asp Thr Gly Thr Tyr Phe Cys
                85                  90                  95

Ala Asn Tyr Gly Trp Gly Tyr Phe Asp Tyr Trp Gly Gln Gly Thr Thr
            100                 105                 110

Leu Thr Val Ser Ser
        115

<210> SEQ ID NO 2
<211> LENGTH: 112
<212> TYPE: PRT
<213> ORGANISM: Mus musculus

<400> SEQUENCE: 2

Asp Val Val Met Thr Gln Thr Pro Leu Ser Leu Pro Val Ser Leu Arg
1               5                   10                  15

Asp Gln Ala Ser Ile Ser Cys Ile Ser Ser Gln Ser Leu Val His Ser
            20                  25                  30

Asn Gly Tyr Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Ala Asp Leu Gly Val Tyr Phe Cys Ser Gln Ser
                85                  90                  95

Thr His Val Pro Tyr Thr Phe Gly Gly Gly Thr Lys Leu Glu Ile Lys
            100                 105                 110

<210> SEQ ID NO 3
<211> LENGTH: 98
<212> TYPE: PRT
<213> ORGANISM: Homo sapiens

<400> SEQUENCE: 3

Gln Val Gln Leu Val Gln Ser Gly Ser Glu Leu Lys Lys Pro Gly Ala
```

```
1               5                   10                  15
Ser Val Lys Val Ser Cys Lys Ala Ser Gly Tyr Thr Phe Thr Ser Tyr
                20                  25                  30

Ala Met Asn Trp Val Arg Gln Ala Pro Gly Gln Gly Leu Glu Trp Met
            35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
                85                  90                  95

Ala Arg
```

<210> SEQ ID NO 4
<211> LENGTH: 100
<212> TYPE: PRT
<213> ORGANISM: Homo sapiens

<400> SEQUENCE: 4

```
Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
                20                  25                  30

Asp Gly Lys Thr Tyr Leu Tyr Trp Tyr Leu Gln Lys Pro Gly Gln Pro
            35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile Gln Leu Pro
            100
```

<210> SEQ ID NO 5
<211> LENGTH: 117
<212> TYPE: PRT
<213> ORGANISM: Artificial Sequence
<220> FEATURE:
<223> OTHER INFORMATION: VH

<400> SEQUENCE: 5

```
Gln Val Gln Leu Val Gln Ser Gly Ser Glu Leu Lys Lys Pro Gly Ala
1               5                   10                  15

Ser Val Lys Val Ser Cys Lys Ala Ser Glu Tyr Ile Phe Thr Asn Tyr
                20                  25                  30

Gly Met Asn Trp Val Lys Gln Ala Pro Gly Gln Gly Phe Glu Trp Met
            35                  40                  45

Gly Trp Ile Asp Thr Asn Thr Gly Glu Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Thr Tyr Tyr Cys
                85                  90                  95

Ala Asn Tyr Gly Trp Gly Tyr Phe Asp Tyr Trp Gly Gln Gly Thr Thr
            100                 105                 110
```

```
Val Thr Val Ser Ser
        115

<210> SEQ ID NO 6
<211> LENGTH: 112
<212> TYPE: PRT
<213> ORGANISM: Artificial Sequence
<220> FEATURE:
<223> OTHER INFORMATION: VL

<400> SEQUENCE: 6

Asp Val Val Met Thr Gln Thr Pro Pro Ser Leu Pro Val Asn Pro Gly
1               5                   10                  15

Glu Pro Ala Ser Ile Ser Cys Arg Ser Ser Gln Ser Leu Val His Ser
            20                  25                  30

Asn Gly Tyr Thr Tyr Leu His Trp Tyr Leu Gln Lys Pro Gly Gln Ser
        35                  40                  45

Pro Gln Leu Leu Ile Tyr Lys Val Ser Asn His Leu Ser Gly Val Pro
    50                  55                  60

Asp Arg Phe Ser Gly Ser Gly Ser Gly Thr Asp Phe Thr Leu Lys Ile
65                  70                  75                  80

Ser Trp Val Glu Ala Glu Asp Val Gly Val Tyr Phe Cys Ser Gln Ser
                85                  90                  95

Thr His Val Pro Tyr Thr Phe Gly Gly Gly Thr Lys Leu Glu Ile Lys
            100                 105                 110

<210> SEQ ID NO 7
<211> LENGTH: 7
<212> TYPE: PRT
<213> ORGANISM: Mus musculus

<400> SEQUENCE: 7

Glu Tyr Ile Phe Thr Asn Tyr
1               5

<210> SEQ ID NO 8
<211> LENGTH: 6
<212> TYPE: PRT
<213> ORGANISM: Mus musculus

<400> SEQUENCE: 8

Asp Thr Asn Thr Gly Glu
1               5

<210> SEQ ID NO 9
<211> LENGTH: 10
<212> TYPE: PRT
<213> ORGANISM: Mus musculus

<400> SEQUENCE: 9

Ala Asn Tyr Gly Trp Gly Tyr Phe Asp Tyr
1               5                   10

<210> SEQ ID NO 10
<211> LENGTH: 11
<212> TYPE: PRT
<213> ORGANISM: Mus musculus

<400> SEQUENCE: 10

Gln Ser Leu Val His Ser Asn Gly Tyr Thr Tyr
1               5                   10
```

```
<210> SEQ ID NO 11
<211> LENGTH: 9
<212> TYPE: PRT
<213> ORGANISM: Mus musculus

<400> SEQUENCE: 11

Ser Gln Ser Thr His Val Pro Tyr Thr
1               5
```

ANTIBODY TARGETING INTERLEUKIN 17A AND PREPARATION METHOD AND APPLICATION THEREOF

CROSS-REFERENCE TO RELATED APPLICATIONS

This application is a national phase application under 35 U.S.C. 371 claiming priority to PCT/CN2018/073458, filed Jan. 19, 2018, which application claims priority to CN 201710602383.3, filed Jul. 21, 2017, the disclosures of which are hereby incorporated by reference in their entireties for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file SequenceListing 1140290.txt, created on May 10, 2019, 7,152 bytes, machine format IBM-PC, MS-Windows operating system, is hereby incorporated by reference in its entirety for all purposes.

FIELD OF THE INVENTION

The present invention relates to the field of medicine, and in particular to an antibody targeted to interleukin 17A (also referred to as IL-17), preparation method and application thereof.

BACKGROUND OF THE INVENTION

So far, 6 members from IL-17 family have been found: IL-17A (IL-17), IL-17B, IL-17C, IL-17D, IL-17E(IL-25) and IL-17F. The interleukins-17 cytokines can bind to the corresponding receptors and mediate different inflammatory responses.

IL-17A was originally discovered to be secreted by activated $CD4^+T$ cell. This type of T cell subset that characteristically secretes IL-17A is called Th17 cells. In addition to Th17 cells, cytotoxicity $CD8^+T$ cell (Tc17), γδT cell, natural killer T cell (NKT-17) and B cells can also express IL-17A under specific conditions. Innate immune cells, including monocytes, neutrophils, natural killer cells, and lymphoid tissue-induced inducer (Lti-like) cells, can also produce IL-17A. Recently, in a study on trypanosome infection, it was found that B cells can also produce IL-17A. Some non-immune cells, such as intestinal Paneth cells and intestinal epithelial cells, can also produce IL-17A under stress. Since the Th17 cells are the most widely distributed in the body and has a wide range of effects in the inflammatory response, it is generally considered to be the main source of IL-17A. The innate cells that produce IL-17A are mainly involved in the host anti-infective immune response as early defense cells of the body.

IL-17A is a homodimer composed of two strands of 155 amino acids linked by a disulfide bond and has a molecular weight of 35 kDa. The structure of IL-17 consists of a 23 amino acid signal peptide (AA) and a 123 amino acid chain region.

The type I cell surface receptor that binds to IL-17 is called IL-17R, and there are at least three of them: IL-17RA, IL-17RB and IL-17RC. IL-17A and IL-17F bind to IL-17RA and IL-17RC receptor complexes in the form of homodimers or heterodimers to transduce signals and participate in autoimmune disease, various inflammatory responses, and host anti-infective immune response. IL-17C binds IL-17RA and IL-17RE receptor complexes to activate downstream signals and promote anti-infective immunity, autoimmune diseases and inflammatory responses. IL-17B was found to bind to IL-17RB, but its downstream signals remain unclear. IL-17RB also forms a receptor complex with IL-17RA to mediate IL-17E-induced type II immune responses. Il-17E was also reported to promote apoptosis in tumor cells. The receptor and downstream signals of IL-17D and the ligand and downstream signals of the orphan receptor IL-17RD are still unclear.

IL-17A mainly induces signal activation of non-hematopoietic-derived cells including epithelial cells and stromal cells. A variety of inflammatory factors and chemokines induced by IL-17A can promote the recruitment of various immune cells, thereby promoting autoimmune diseases. Studies have found that IL-17A and IL-17F, and their major secretory T cell subpopulations, Th17 cells, also play important roles in a variety of autoimmune diseases, including autoimmune diseases, such as rheumatoid arthritis (RA) and multiple sclerosis (MS), as well as inflammatory bowel disease (IBD), psoriasis systemic lupus erythematosus (SLE) and type 1 diabetes (T1D).

IL-17A and IL-17F exert their functions of promoting inflammatory response mainly by inducing target cells to express various inflammatory factors and chemokines. IL-17A binds to the cell surface receptor IL-17RA and recruits IL-17RC to form a heterodimer that mediates downstream signaling pathways. IL-17 binds to its receptor and activates TRAF6 (TNF-receptor associated factor 6). IL-17 shares the same transcriptional pathway as IL-1 and TNF, which activates NF-kB and three MAP (mitogen-activated protein) enzymes, including ERK1, ERK2, JNK, p38. The pathways are found in both synoviocytes and chondrocytes.

Therefore, in view of the role and function of IL-17A in various related diseases, there remains a need in the art to develop improved anti-IL-17 specific antibodies suitable for treating patients.

SUMMARY OF INVENTION

The purpose of the present invention is to provide an antibody against IL-17A, a preparation method and application thereof.

In the first aspect of the invention, a heavy chain variable region of an antibody is provided, wherein the heavy chain variable region comprise three complementary determining regions CDR:

CDR1 as shown in SEQ ID NO: 7,
CDR2 as shown in SEQ ID NO: 8 and
CDR3 as shown in SEQ ID NO: 9.

In another preferred embodiment, any one of the above amino acid sequences further includes a derivative sequence which is obtained through optional addition, deletion, modification and/or substitution of at least one (such as 1-3, preferably 1-2, more preferably 1) amino acid and is capable of retaining IL-17A binding affinity.

In another preferred embodiment, the heavy chain variable region further comprises a FR region of human or a FR region of mouse.

In another preferred embodiment, the heavy chain variable region has the amino acid sequence as shown in SEQ ID NO: 1.

In another preferred embodiment, the heavy chain variable region has the amino acid sequence as shown in SEQ ID NO: 5.

In the second aspect of the invention, a heavy chain of an antibody is provided, wherein the heavy chain has a heavy chain variable region according to the first aspect of the present invention.

In another preferred embodiment, the heavy chain of the antibody further comprises a heavy chain constant region.

In another preferred embodiment, the heavy chain constant region is of human, mouse or rabbit.

In the third aspect of the invention, a light chain variable region of an antibody is provided, wherein the light chain variable region comprise three complementary determining regions CDR:

CDR1' as shown in SEQ ID NO: 10,
CDR2' with the amino acid sequence of KVS, and
CDR3' as shown in SEQ ID NO: 11.

In another preferred embodiment, any one of the above amino acid sequences further includes a derivative sequence which is obtained through optional addition, deletion, modification and/or substitution of at least one (such as 1-3, preferably 1-2, more preferably 1) amino acid and is capable of retaining IL-17A binding affinity.

In another preferred embodiment, the light chain variable region further comprises a FR region of human or a FR region of mouse.

In another preferred embodiment, the light chain variable region has the amino acid sequence as shown in SEQ ID NO: 2.

In another preferred embodiment, the light chain variable region has the amino acid sequence as shown in SEQ ID NO: 6.

In the fourth aspect of the invention, a light chain of an antibody is provided, wherein the light chain has a light chain variable region according to the third aspect of the present invention.

In another preferred embodiment, the light chain of the antibody further comprises a light chain constant region.

In another preferred embodiment, the light chain constant region is of human, mouse or rabbit.

In a fifth aspect of the invention, an antibody is provided, wherein the antibody has:

(1) a heavy chain variable region according to the first aspect of the present invention; and/or
(2) a light chain variable region according to the third aspect of the present invention;

or, the antibody has: a heavy chain according to the second aspect of the present invention; and/or a light chain according to the fourth aspect of the present invention.

In another preferred embodiment, the antibody has an affinity to the human IL-17A protein (preferably wild type) with an $EC_{50}$ of 5-50 ng/ml.

In another preferred embodiment, the antibody has an affinity to the human IL-17A protein (preferably wild type) with an $EC_{50}$ of 15.4 ng/ml.

In another preferred embodiment, the antibody is selected from an animal-derived antibody, a chimeric antibody, a humanized antibody, or a combination thereof.

In another preferred embodiment, the antibody is a double chain antibody, or a single chain antibody.

In another preferred embodiment, the antibody is a monoclonal antibody.

In another preferred embodiment, the antibody is a partially or fully humanized monoclonal antibody.

In another preferred embodiment, the heavy chain variable region sequence of the antibody is as shown in SEQ ID NO.: 1 or 5; and/or
the light chain variable region sequence of the antibody is as shown in SEQ ID NO.: 2 or 6.

In another preferred embodiment, the heavy chain variable region sequence of the antibody is as shown in SEQ ID NO.: 1; and the light chain variable region sequence of the antibody is as SEQ ID NO.: 2.

In another preferred embodiment, the heavy chain variable region sequence of the antibody is as shown in SEQ ID NO.: 5; and the light chain variable region sequence of the antibody is as SEQ ID NO.: 6.

In another preferred embodiment, the antibody is in the form of a drug conjugate.

In a sixth aspect of the invention, a recombinant protein is provided, wherein the recombinant protein has:

(i) the heavy chain variable region according to the first aspect of the present invention, the heavy chain according to the second aspect of the present invention, the light chain variable region according to the third aspect of the present invention, the light chain according to the fourth aspect of the present invention, or the antibody according to the fifth aspect of the present invention; and (ii) optionally a tag sequence that assist in expression and/or purification.

In another preferred embodiment, the tag sequence comprises 6His tag.

In another preferred embodiment, the recombinant protein (or polypeptide) includes a fusion protein.

In another preferred embodiment, the recombinant protein is a monomer, a dimer, or a multimer.

In a seventh aspect of the invention, a CAR construct is provided, wherein the scFV segment of the monoclonal antibody antigen binding region of the CAR construct is a binding region that specifically binds to IL-17A, and the scFv has the heavy chain variable region according to the first aspect of the invention and the light chain variable region according to the third aspect of the invention.

In an eighth aspect of the invention, a recombinant immune cell is provided, wherein the immune cell expresses an exogenous CAR construct according to the seventh aspect of the invention.

In another preferred embodiment, the immune cells are selected from the group consisting of NK cells and T cells.

In another preferred embodiment, the immune cells are from a human or non-human mammal (e.g., a mouse).

In a ninth aspect of the invention, an antibody drug conjugate is provided, which comprises:

(a) an antibody moiety selected from the heavy chain variable region according to the first aspect of the invention, the heavy chain according to the second aspect of the invention, the light chain variable region according to the third aspect of the invention, the light chain according to the fourth aspect of the invention, the antibody according to the fifth aspect of the invention, or a combination thereof and (b) a coupling moiety coupled to the antibody moiety, the coupling moiety being selected from a detectable label, a drug, a toxin, a cytokine, a radionuclide, an enzyme, or a combination thereof.

In another preferred embodiment, the antibody moiety is coupled to the coupling moiety via a chemical bond or linker.

In a tenth aspect of the invention, the use of an active ingredient is provided, wherein the active ingredient is selected from the heavy chain variable region according to the first aspect of the invention, the heavy chain according to the second aspect of the invention, the light chain variable region according to the third aspect of the invention, the light chain according to the fourth aspect of the invention, or the antibody according to the fifth aspect of the invention, the recombinant protein according to the sixth aspect of the present invention, the immunological cell according to the eighth aspect of the present invention, the antibody drug conjugate according to the ninth aspect of the present invention, or a combination thereof, and the active ingredient is used for (a) preparing a detection reagent or kit; and/or (b) preparing a medicament for the prevention and/or treatment of IL-17A related diseases.

In another preferred embodiment, the active ingredient is used for preventing and/or treating a disease related to IL-17A.

In another preferred embodiment, the disease related to IL-17A is selected from inflammation, autoimmune disease, or a combination thereof; preferably an autoimmune disease.

In another preferred embodiment, the diseases are selected from psoriasis, psoriatic arthritis, ankylosing spondylitis, multiple sclerosis, inflammatory arthritis, or a combination thereof, preferably inflammatory arthritis.

In another preferred embodiment, the inflammatory arthritis is selected from osteoarthritis, rheumatoid arthritis, rheumatic arthritis, or a combination thereof, preferably rheumatic arthritis.

In another preferred embodiment, the antibody is in the form of a drug conjugate (ADC).

In another preferred embodiment, the detection reagent or kit is used for diagnosing diseases related to IL-17A.

In another preferred embodiment, the detection reagent or kit is used for detecting IL-17A protein in a sample.

In another preferred embodiment, the detection reagent is a test strip.

In an eleventh aspect of the invention, a pharmaceutical composition is provided, which comprises:

(I) an active ingredient, which is selected from the heavy chain variable region according to the first aspect of the invention, the heavy chain according to the second aspect of the invention, the light chain variable region according to the third aspect of the invention, the light chain according to the fourth aspect of the invention, or the antibody according to the fifth aspect of the invention, the recombinant protein according to the sixth aspect of the present invention, the immunological cell according to the eighth aspect of the present invention, the antibody drug conjugate according to the ninth aspect of the present invention, or a combination thereof; and (ii) a pharmaceutically acceptable carrier.

In another preferred embodiment, the pharmaceutical composition is in the form of a liquid formulation.

In another preferred embodiment, the pharmaceutical composition is in the form of an injection.

In a twelfth aspect of the invention, a polynucleotide is provided, which encodes a polypeptide selected from (1) the heavy chain variable region according to the first aspect of the present invention, the heavy chain according to the second aspect of the present invention, the light chain variable region according to the third aspect of the present invention, the light chain according to the fourth aspect of the present invention, or the antibody according to the fifth aspect of the present invention; or (2) the recombinant protein according to the sixth aspect of the invention;

(3) the CAR construct according to the seventh aspect of the invention.

In a thirteenth aspect of the invention, a vector is provided, which comprises the polynucleotide according to the twelfth aspect of the invention.

In another preferred embodiment, the carrier includes a bacterial plasmid, phage, yeast plasmid, plant cell virus and mammalian cell virus, for instance adenovirus, retrovirus or other carriers.

In a fourteenth aspect of the invention, a genetically engineered host cell is provided, which comprises the vector according to the thirteenth aspect of the invention or has the polynucleotide according to the twelfth aspect of the invention integrated into its genome.

In a fifteenth aspect of the invention, a method for in vitro detecting (including diagnostic or non-diagnostic) IL-17A protein in a sample is provided, wherein the method comprises the steps of:

(1) in vitro contacting a sample with the antibody according to the fifth aspect of the invention;

(2) detecting whether an antigen-antibody complex is formed, wherein the formation of the complex indicates the presence of a IL-17A protein in the sample.

In a sixteenth aspect of the invention, a detection plate is provided, which comprises: a substrate (support chip) and a testing strip, wherein the testing strip contain the antibody according to the fifth aspect of the present invention or the immuneconjugate according to the ninth aspect of the present invention.

In a seventeenth aspect of the invention, a reagent kit is provided, which comprises:

(1) a first container containing the antibody according to the fifth aspect of the invention; and/or (2) a second container containing a second antibody against the antibody according to the fifth aspect of the invention;

or the reagent kit comprises the detection plate according to the sixteenth aspect of the present invention.

In an eighteenth aspect of the invention, a preparation method for a recombinant polypeptide is provided, which comprises:

(a) culturing the host cell according to the fourteenth aspect of the invention under a condition suitable for expression;

(b) isolating the recombinant polypeptide from the culture, wherein the recombinant polypeptide is the antibody according to the fifth aspect of the present invention or the recombinant protein according to the sixth aspect of the present invention.

In a nineteenth aspect of the invention, a method for a disease related to IL-17A is provided, wherein the method comprises administering to a subject in need thereof an antibody according to the fifth aspect of the invention, an antibody-drug conjugate of the antibody, or a CAR-T cell expressing the antibody, or a combination thereof.

It should be understood that, within the scope of the present invention, the technical features specifically described above and below (such as in the Examples) can be combined with each other, thereby constituting a new or preferred technical solution which needs not be described one by one.

DESCRIPTION OF THE DRAWINGS

FIG. 1 shows the effects of dexamethasone and humanized anti-IL-17A antibody on imiquimod-induced psoriasis in mice.

DETAILED DESCRIPTION OF THE INVENTION

Through extensive and intensive researches, the inventors have unexpectedly obtained an anti-IL-17A monoclonal antibody having extremely excellent affinity and specificity through extensive screening, and a humanized antibody obtained based on the antibody. The antibody of the present invention is capable of binding specifically to the IL-17A antigen with high affinity (the $EC_{50}$ determined by ELISA is about 15.4 ng/ml) and significantly inhibits the binding of IL-17A to the IL-17 receptor without any visible side effects to the mammal itself. The present invention has been completed on the basis of this.

Term

As used herein, the term "conjugate" refers to a soluble receptor or a fragment thereof or analog thereof, or an antibody or fragment thereof or analog thereof, that is capable of binding to a target. The "IL-17A conjugate" as used in the present invention refers to an antibody or a fragment thereof or an analog thereof which is capable of specifically recognizing IL-17A and binds to IL-17A.

As used herein, the terms "administration" and "treatment" mean that an exogenous medicament, therapeutic agent, diagnostic agent or composition is applied to an animal, human, subject, cell, tissue, organ or biological fluid. "Administration" and "treatment" can refer to therapeutics, pharmacokinetics, diagnostics, research, and experimental methods. Treatment of cells includes contacting a reagent with the cells, as well as contacting a reagent with a fluid, where the fluid is in contact with the cells. "Administration" and "treatment" also mean in vitro and ex vivo treatments by a reagent, diagnostic, binding compound, or by another cell.

"Treatment", as it applies to a human, animal or research subject, refers to therapeutic treatment, prophylactic or preventive measures, research and diagnosis; which includes contact of IL-17A conjugate with humans or animals, subjects, cells, tissues, physiological compartments or physiological fluids.

As used herein, the term "treat" means that a therapeutic agent for internal or external comprising any of the IL-17A conjugates of the present invention or compositions thereof is administered to a patient having one or more diseases symptoms on which the therapeutic agent has known therapeutic activity. Typically, the therapeutic agent is administered to the patient in an amount (a therapeutically effective amount) effective to alleviate one or more diseases symptoms.

As used herein, the term "optional" or "optionally" means that the described event or situation can but does not necessarily occur. For example, "optionally comprising 1-3 antibody heavy chain variable regions" means that the antibody heavy chain variable region with specific sequence can be, but not necessarily be present, and there may be one, two or three antibody heavy chain variable regions.

Antibody

As used herein, the term "antibody" refers to an immunoglobulin, a tetra-peptide chain structure connected together by disulfide bonds between two identical heavy chains and two identical light chains. Immunoglobulin heavy chain constant regions exhibit different amino acid compositions and orders, hence present different kinds of antigenicity. Accordingly, immunoglobulins can be divided into five categories, or referred to as immunoglobulin isotypes, namely IgM, IgD, IgG, IgA and IgE, the corresponding heavy chains are μ chain, δ chain, γ chain, α chain and ε chain, respectively. IgG represents the most important class of immunoglobulins, which can be further divided into 4 subclasses based on differences in chemical structure and biological function: IgG1, IgG2, IgG3 and IgG4. Light chain can be divided into κ or λ chain based on different constant regions. The subunit structures and 3D configurations of different immunoglobulins are well known to those skilled in the art.

Sequences of about 110 amino acid adjacent to the N-terminus of the antibody heavy and light chains are highly variable, known as the variable region (V region); the rest of the amino acid sequences near the C-terminus are relatively stable, known as the constant region (C region). Variable region comprises three hypervariable regions (HVR) and four relatively conserved framework regions (FR). The amino acid sequences of the four FRs are relatively conservative and are not directly involved in the binding reaction. The three hypervariable regions determine the specificity of the antibody, also known as complementarity determining region (CDR). Each light chain variable region (LCVR) and each heavy chain variable region (HCVR) is composed of three CDR regions and four FR regions, with sequential order from the amino terminus to the carboxyl terminus being: FR1, CDR1, FR2, CDR2, FR3, CDR3, and FR4. The three light chain CDRs, i.e., light chain hypervariable region (LCDR), refer to LCDR1, LCDR2, and LCDR3; and the three heavy chain CDRs, i.e., heavy chain hypervariable region (HCDR), refer to HCDR1, HCDR2 and HCDR3. The number and location of CDR region amino acid residues in LCVR and HCVR regions of the antibody or antigen binding fragment herein comply with the known Kabat numbering criteria (LCDR1-3, HCDE2-3), or comply with Kabat and Chothia numbering criteria (HCDR1). The four FR regions of the natural heavy and light chain variable regions are in a substantially β-folded configuration, and are linked by three CDRs that form the linker ring and, in some cases, form a partial β-folded structure. The CDRs in each chain stand are brought together through FR regions and form the antigen-binding site of the antibody together with the CDRs of the other chain. It is possible to determine which amino acids constitute the FR or CDR regions by comparing the amino acid sequences of the same type of antibody. Constant regions are not directly involved in the binding of the antibodies to the antigens, but they exhibit different effector functions, such as antibody-dependent cytotoxicity involved in antibodies.

As used herein, the term "antigen-binding fragment" refers to Fab fragment, Fab' fragment, F(ab')2 fragment or a single Fv fragment with antigen-binding activity. Fv antibody is a minimum antibody fragment comprising the antibody heavy chain variable region, light chain variable region, and all antigen-binding sites without the constant region. Generally, Fv antibody further comprises a polypeptide linker between the VH and VL domains and is capable of forming a structure required for antigen binding.

As used herein, the term "antigenic determinant" refers to discontinuous, three-dimensional sites on the antigen, recognized by the antibody or the antigen-binding fragment of the present invention.

The present invention includes not only intact antibodies but also fragments of antibodies or fusion proteins formed by antibodies with other sequences with immunological activity. Accordingly, the present invention also includes fragments, derivatives and analogs of said antibodies.

In the present invention, antibodies include murine, chimeric, humanized or fully human antibodies prepared by techniques well known to those skilled in the art. Recombinant antibodies, such as chimeric and humanized monoclonal antibodies, including both human and non-human portions, can be prepared using recombinant DNA techniques known in the art.

As used herein, the term "monoclonal antibody" refers to an antibody that is secreted from a clone derived from a single cell. The monoclonal antibodies are highly specific and target a single antigenic epitope. The cell may be a eukaryotic, prokaryotic or phage clonal cell line.

As used herein, the term "chimeric antibody" is an antibody molecule expressed by a host cell transfected with a vector into which a chimeric gene formed by splicing a V region gene of a mouse antibody and a C region gene of a human antibody is inserted. It not only retains the high specificity and affinity of the parental mouse antibody, but also enables its human Fc segment to effectively mediate biological effects.

As used herein, the term "humanized antibody", is a variant of a variable region of the mouse antibody of the invention, having a CDR region derived from (derived substantially from) a non-human antibody (preferably a mouse monoclonal antibody), and an FR region and a constant region derived substantially from a human antibody sequence. The CDR region sequences of the mouse antibodies are grafted onto the framework sequences of different types of human germline antibodies. Because the CDR sequence is responsible for most of the antibody-antigen interactions, recombinant antibody that mimics the properties of a particular naturally occurring antibody can be expressed by constructing an expression vector.

In the present invention, antibodies may be monospecific, bispecific, trispecific, or more multiplex specific antibodies.

In the present invention, the antibody of the present invention also includes conserved variants of the antibodies of the present invention, refers to the polypeptides formed by replacing at most 10, preferably at most 8, more preferably at most 5, and most preferably 3 amino acid of the amino acid sequence of the polypeptide of the present invention with the amino acid having similar or analogous properties. These conservative variant polypeptides are preferably formed by carrying out the amino acid substitution according to Table A.

TABLE A

| Initial residue | Representative substitution | Preferred substitution |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

Anti IL-17A Antibody

As used herein, the term "IL-17A" generally refers to a natural or recombinant human IL-17A, as well as a non-human homolog of human IL-17A. Unless otherwise indicated, the molar concentration of IL-17A was calculated using the molecular weight of the homodimer of IL-17A (for example, for human IL-17A is 30 KDa).

As used herein, the term "human IL-17A (huIL-17A)" refers to the mature form of human IL-17A protein with accession numbers NP-002180 and AAT22064 (i.e., residues 24-155), as well as natural variants and polymorphisms thereof.

In the present invention, an antibody with high specificity and high affinity for IL-17A is provided, which comprises a heavy chain and a light chain, wherein the heavy chain comprises a heavy chain variable region (VH) amino acid sequence and the light chain comprises a light chain variable region (VL) amino acid sequence.

Preferably, the respective CDRs of the heavy chain variable region (VH) amino acid sequence and the light chain variable region (VL) the amino acid sequence are selected from the group consisting of:
a1) SEQ ID No.: 7;
a2) SEQ ID No.: 8;
a3) SEQ ID No.: 9;
a4) SEQ ID No.: 10;
a5) KVS;
a6) SEQ ID No.: 11;
a7) A sequence having IL-17A binding affinity formed by adding, deleting, modifing, and/or substituting at least one (such as 1-5, 1-3, preferably 1-2, more preferably 1) amino acid from any one of the above amino acid sequences.

In another preferred embodiment, the sequence formed by addition, deletion, modification and/or substitution of at least one amino acid sequence is preferably an amino acid sequence having at least 80%, preferably at least 85%, more preferably at least 90%, most preferably at least 95% of homology.

The antibody of the present invention may be a double-stranded or single-chain antibody, and may be selected from an animal-derived antibody, a chimeric antibody, a humanized antibody, more preferably a humanized antibody, a human-animal chimeric antibody, more preferably a fully humanized antibody.

The antibody derivative of the present invention may be a single-chain antibody, and/or an antibody fragment, such as Fab, Fab', (Fab') 2 or other known antibody derivatives in the art and the like, as well as any one or more of an antibody of IgA, IgD, IgE, IgG and IgM antibodies or other subtypes of antibodies.

Among them, the animal is preferably a mammal, such as a mouse.

The antibody of the invention may be a murine antibody, chimeric antibody, humanized antibody, CDR grafted and/or or modified antibody that targets human IL-17A.

In a preferred embodiment of the invention, any one or more of the above SEQ ID No.: 7, 8 and 9, or a sequence having IL-17A binding affinity formed by adding, deleting, modifying and/or substituting at least one amino acid is located in the CDR region of the heavy chain variable region (VH).

In a preferred embodiment of the invention, any one or more of the above SEQ ID No.: 10, amino acid sequence: KVS and SEQ ID No.: 11, or a sequence having IL-17A binding affinity formed by adding, deleting, modifying and/or substituting at least one amino acid is located in the CDR region of the light chain variable region (VL).

In a more preferred embodiment of the invention, the VH CDR1, CDR2, CDR3 is independently selected from any one or more of SEQ ID No.: 7, 8 and 9, or a sequence having IL-17A binding affinity formed by adding, deleting, modifying and/or substituting at least one amino acid; the VL CDR1, CDR2, CDR3 is independently selected from any one or more of SEQ ID No.: 10, amino acid sequence: KVS and SEQ ID No.: 11, or a sequence having IL-17A binding affinity formed by adding, deleting, modifying and/or substituting at least one amino acid.

In the above aspect of the invention, the number of added, deleted, modified and/or or substituted amino acids is preferably not more than 40%, more preferably not more than 35%, more preferably 1-33%, more preferably 5-30%, more preferably 10-25%, more preferably 15-20% of the total amino acid number of the initial amino acid sequence.

In the present invention, the number of amino acids added, deleted, modified and/or substituted is usually 1, 2, 3, 4 or 5, preferably 1-3, more preferably 1-2, most preferably 1.

Antibody Preparation

Any method suitable for the production of monoclonal antibodies can be used to produce the anti-IL-17A antibodies of the invention. For example, an animal can be immunized with a linked or naturally occurring IL-17A homodimer or a fragment thereof. Suitable immunization methods can be used, including adjuvants, immunostimulants, repeated enhanced immunizations, and one or more routes can be used.

Any suitable form of IL-17 can be used as an immunogen (antigen) for the production of a non-human antibody specific for IL-17A and for screening for the biological activity of the antibody. The stimulating immunogen can be a full-length mature human IL-17A, including a natural homodimer, or a peptide containing a single/multiple epitopes. The immunogen can be used alone or in combination with one or more immunogenic enhancers known in the art. The immunogen can be purified from natural sources or produced in genetically modified cells. DNA encoding the immunogen may be derived from genomic or non-genomic (for example cDNA). The DNA encoding an immunogen can be expressed using a suitable genetic vector including, but not limited to an adenoviral vector, an adeno-associated viral vector, a baculovirus vector, a plasmid and a non-viral vector.

Exemplary methods for producing anti-human IL-17A antibody of the invention are described in the Examples 1.

Humanized antibodies can be selected from any class of immunoglobulins, including IgM, IgD, IgG, IgA and IgE. In the present invention, the antibody is an IgG antibody, and an IgG1 subtype is used. Optimization of the necessary constant domain sequences is readily achieved by screening antibodies using the biological assays described in the examples below to produce the desired biological activity.

Likewise, any type of light chain can be used in the compounds and methods herein. Specifically, a κ, λ chain or variant thereof is useful in the compounds and methods of the invention.

Exemplary methods for humanizing the anti-human IL-17A antibody of the invention are described in the examples 4.

The sequence of the DNA molecule of the antibody or fragment thereof of the present invention can be obtained by a conventional technique such as PCR amplification or genomic library screening. In addition, the coding sequences of the light chains and heavy chains can also be fused together to form a single chain antibody.

Once the relevant sequence is obtained, the relevant sequence can be obtained in bulk using the recombination method. It is usually cloned into a vector, transferred to a cell, and then isolated from the host cell after proliferation by conventional methods.

In addition, synthetic methods can also be used to synthesize relevant sequences, especially when the fragment length is short. Usually, a fragment of long sequence can be obtained by first synthesizing a plurality of small fragments and then connecting them. The DNA sequence can then be introduced into a variety of existing DNA molecules (or vectors) and cells known in the art.

The present invention also relates to a vector comprising the suitable DNA sequence as described above and a suitable promoter or control sequence. These vectors can be used to transform suitable host cells to enable them to express proteins.

Host cells can be prokaryotic cells, such as bacterial cells; or lower eukaryotic cells, such as yeast cells; or higher eukaryotic cells, such as mammalian cells. Preferred animal cells include (but not limited to): CHO-S, CHO-K1 and HEK-293 cells.

The step of transforming a host cell with recombinant DNA as described in the present invention can be carried out by techniques well known in the art. The obtained transformants can be cultured in a conventional manner to express the polypeptides encoded by the genes of the present invention. Depending on the host cell used, it is cultured under appropriate conditions using a conventional medium.

Typically, the resulting host cells are cultured under conditions suitable for expression of the antibodies of the invention. The antibody of the present invention is then purified using a conventional immunoglobulin purification step, such as protein A-Sepharose, hydroxyapatite chromatography, gel electrophoresis, dialysis, ion exchange chromatography, hydrophobic chromatography, molecular sieve chromatography or affinity chromatography, and conventional separation and purification means well known to those skilled in the art.

The resulting monoclonal antibodies can be identified by conventional means. For example, the binding specificity of a monoclonal antibody can be determined by immunoprecipitation or in vitro binding assays (such as radioimmunoassay (RIA) or enzyme-linked immunosorbent assay (ELISA)).

Application

In the invention, the use of the antibody of the invention is provided, for example, for the preparation of diagnostic formulations, or for the preparation of a medicine for the prevention and/or treatment of IL-17A related diseases. The IL-17A related diseases include inflammatory diseases, autoimmune diseases, and the like, including but not limited to psoriasis, psoriatic arthritis, ankylosing spondylitis, multiple sclerosis, inflammatory bowel disease (such as Crohn's disease, ulcerative colitis, and the like), osteoarthritis, rheumatoid arthritis (RA), rheumatic arthritis or osteoporosis, inflammatory fibrosis (such as scleroderma, pulmonary fibrosis and sclerosis), asthma (including allergic asthma), allergic reaction and cancer.

Pharmaceutical Composition

The present invention also provides a composition. In a preferred embodiment, the composition is a pharmaceutical composition comprising the above-described antibody or active fragment thereof or a fusion protein thereof or an ADC thereof or corresponding CAR-T cell, and a pharmaceutically acceptable carrier. In general, these materials may be formulated in a non-toxic, inert and pharmaceutically acceptable aqueous carrier medium, wherein the pH is generally about 5 to 8, preferably about 6 to 8, although the pH may vary depending on the nature of the substance to be formulated, and the condition to be treated. The formulated pharmaceutical compositions may be administered by conventional routes, including, but not limited to, intratumoral, intraperitoneal, intravenous, or local drug delivery.

The antibody of the present invention may also be expressed from a nucleotide sequence in a cell for cell therapy, for example, the antibody is used for a chimeric antigen receptor T cell immunotherapy (CAR-T) and the like.

The pharmaceutical compositions of the present invention can be used directly to bind with IL-17A protein molecules and are therefore useful for the prevention and treatment of IL-17A related diseases. In addition, other therapeutic agents may be used at the same time.

The pharmaceutical composition of the present invention contains a monoclonal antibody (or a conjugate thereof) of the present invention in a safe and effective amount (e.g., 0.001 to 99 wt % by weight, preferably 0.01 to 90 wt % by weight, more preferably 0.1 to 80 wt % by weight) and an acceptable carrier or excipient. Such carriers include, but are not limited to, saline, buffer, glucose, water, glycerol, ethanol, and combinations thereof. The pharmaceutical preparation should match the method of administration. The pharmaceutical compositions of the present invention may be prepared into the form of injections, for example, saline or aqueous solutions containing glucose and other adjuvants are prepared by conventional methods. Pharmaceutical compositions such as injections, solutions should be made under aseptic conditions. The amount of the active ingredient is a therapeutically effective amount, such as about 1 microgram/kg body weight per day to about 5 mg/kg body weight per day. In addition, the polypeptides of the present invention may also be used with other therapeutic agents.

When a pharmaceutical composition is used, a safe and effective amount of an immunoconjugate is administered to a mammal wherein the safe effective amount is generally at least about 10 micrograms per kilogram of body weight and, in most cases, no more than about 50 milligrams per kilogram of body weight, preferably, the dose is from about 10 micrograms per kilogram body weight to about 20 milligram per kilogram of body weight. Of course, the route of administration, the patient's health and other factors, should be considered for the specific dose, which are within the scope of skills of skilled practitioners.

Detection Use and Kit

The antibodies of the present invention can be used in detection applications, for example for detecting samples to provide diagnostic information.

In the present invention, the samples used include cells, tissue samples, and biopsy specimens. The term "biopsy" used in the present invention should include all types of biopsy known to those skilled in the art. Thus, the biopsies used in the present invention may include a tissue sample prepared, for example, by endoscopic methods or punch- or needle-biopsies of organs.

The samples used in the present invention include fixed or preserved cells or tissue samples.

The present invention also provides a kit containing an antibody (or a fragment thereof) of the present invention. In a preferred embodiment of the present invention, the kit further comprises a container, an instruction for use, a buffer agent and so on. In a preferred embodiment, the antibody of the invention may be immobilized on a test plate.

The Main Advantages of the Present Invention (a) The antibody of the present invention has excellent biological activity and specificity and has high affinity (The $EC_{50}$ can be as high as about 10-20 ng/ml by ELISA). In addition, it has a good binding affinity for IL-17A, and can not bind to other family members IL-17B, IL-17D, IL-17E and IL-17F, and can be used as an antibody targeting IL-17A.

(b) The humanized antibody of the present invention not only has better affinity for IL-17A but also has lower immunogenicity than the murine antibody.

(c) The antibody of the present invention significantly inhibits the binding of IL-17A to the IL-17 receptor without any visible toxic side effects to the mammal itself.

(d) The antibodies of the present invention have a certain affinity for IL-17A of some non-human mammals, thereby facilitating testing and quality control in animal models.

The present invention will be further illustrated below with reference to the specific examples. It should be understood that these examples are only to illustrate the invention but not to limit the scope of the invention. The experimental methods with no specific conditions described in the following examples are generally performed under the conventional conditions such as the conditions described in J. Sambrook et al., Molecular Cloning: A Laboratory Manual (New York: Cold Spring Harbor Laboratory Press, 1989), or according to the manufacturer's instructions. Unless indicated otherwise, parts and percentage are weight parts and weight percentage.

EXAMPLES 1

Method for Preparing Anti-Human IL-17A Mouse Monoclonal Antibody—Original Antibody 1.1 Preparation of Hybridoma Cells Producing Murine Monoclonal Antibodies Firstly, human IL-17A protein used as an antigen was emulsified with an adjuvant, and was used for multi-point subcutaneous immunization of BALB/c mice, and the serum titer of the immunized mice was monitored. After reaching the requirement, the mice spleen cells were fused with myeloma (Sp2/0) cells, and hybridoma polyclonal cells were obtained by HAT screening.

1.2 Indirect ELISA—Screening Method for Hybridoma Cells

The polyclonal antibody with high specific binding was screened by ELISA and monoclonal culture was performed, and the monoclonal cell lines with high specific binding were screened by ELISA method; monoclonal cell lines with cytofunctional effects were screened through IL-6 release assay by using HT1080 cells. The affinity and half-life were then analyzed by Biacore method to finally obtain monoclonal cells expressing IL-17A.

Experiment Material:

Recombinant Human IL-17A, Sino Biological, 12047-HNAS

Experiment Method:

Human IL-17A was formulated into a 1 μg/ml coating solution with CBS, and added to the ELISA plate at 50 μL/well, and the plate was coated at 2 to 8° C. for 12 hours or longer. The residue coating solution was discarded, 3% milk was added, 200 μL per well, and the plate was blocked at room temperature for 1 hour. Each well was washed with not less than 200 μL of PBST, and the hybridoma supernatant was diluted to 100 μg/ml, and was 10-fold diluted for 10 gradients, and added to the plate at 100 μL/well. After incubating for 1 hour at room temperature, each well was added with not less than 200 μL of PBST and washed 4 times, and then 100 μL/well of HRP-conjugated goat anti-mouse IgG Fc (purchased from Jackson Inc.) diluted 25,000 times with 3% milk-PBST was added. After incubating for 1 hour at room temperature, each well was added with not less than 200 μL of PBST and washed 4 times, and patted to dryness. TMB development solution was added at 100 μL per well. After reacting for 5 minutes at room temperature, the reaction was quenched by adding 2M $H_2SO_4$ at 50 μL/well. After the reaction was quenched, the ELISA plate was placed on a microplate reader, and the absorbance OD450 value was read at a wavelength of 450 nm.

Experiment Results:

TABLE 1

Comparison of the binding activity of hybridomas to human IL-17a

| sample name | $EC_{50}$ (ng/mL) |
|---|---|
| 1B1/7A2 | 310.9 |
| 1B1/7C8 | 214.6 |
| 7D6/5H8 | 194.4 |
| 7D6/6B11 | 210.1 |
| 7D6/6G11 | 226.4 |
| 1B1/8E1 | 268.9 |
| 1B1/8E5 | 448.2 |

It can be seen from Table 1 that among the selected antibodies, the hybridoma 14F10/9F6 (or the antibody produced thereof) has a very high binding activity to human IL-17a.

EXAMPLES 2

Anti-IL-17A Antibody V-Gene Sequence Cloning

Based on the 5'RACE technique, the DNA sequence encoding the variable region of a mouse antibody expressed by hybridoma 7D6/5H8 was determined. Briefly, gene-specific cDNAs for heavy and light chains were prepared using SMART 5' RACE Synthesis Kit (TAKARA, No. 634859) according to the manufacturer's instructions. The PCR product was analyzed by agarose gel electrophoresis. The variable region size of both heavy and light chains is approximately 500 base pairs. The amplified PCR product with the appropriate size obtained from the reaction was cloned into the vector pEASY-Blunt Simple plasmid (Beijing TransGen, No. CB111-02), and transformed into Stellar E. coli competent cells (TAKARA, No. 636763). Clones were screened by colony PCR using universal M13 forward or reverse primers, and 2-3 clones were selected from each reaction for DNA sequencing analysis. Each sequencing reaction result of each clone was analyzed using the Expasy-translation tool. The sequencing results showed that the anti-IL17A antibody V region sequence expressed by 7D6/5H8 was as follows:

IL17-HC1
SEQ ID NO: 1
QIQLVQSGPELKKPGETVKISCKAS<u>EYIFTNY</u>GMNWVKEAPGKAFKWM

GW<u>IDTNTGE</u>PTYAEDFKGRFAFSLDSSATSAFLQISNLKDDDTGTYFC

<u>ANYGWGYFDY</u>WGQGTTLTVSS in which, the underlined portions are CDR1, CDR2, and CDR3 (SEQ ID NO.: 7, 8, and 9).

IL17-LC1
SEQ ID NO: 2
DVVMTQTPLSLPVSLRDQASISCISS<u>QSLVHSNGYTY</u>LHWYLQKPGQS

PKLLIY<u>KVS</u>NRFSGVPDRFSGSGSGTDFTLKISRVEAADLGVYFC<u>SQS</u>

<u>THVPYT</u>FGGGTKLEIK in which, the underlined portions are CDR1', CDR2', and CDR3' (SEQ ID NO.: 10, amino acid sequence: KVS and SEQ ID NO.: 11).

TABLE 2

CDR secuence of mouse anti-IL-17A antibody

| Domain | | sequence | SEQ ID NO |
|---|---|---|---|
| VH | CDR1 | EYIFTNY | 7 |
| | CDR2 | DTNTGE | 8 |
| | CDR3 | ANYGWGYFDY | 9 |
| VL | CDR1' | QSLVHSNGYTY | 10 |
| | CDR2' | KVS | — |
| | CDR3' | SQSTHVPYT | 11 |

EXAMPLES 3

Construction and Expression of Chimeric Antibodies 3.1 Preparation of Chimeric Antibodies Chimeric heavy and light chains were constructed by ligating mouse 7D6/5H8 VH and VL region cDNA cloned by PCR to human IgG1 and k constant regions, respectively. The 5' and 3' ends of the mouse cDNA sequence were modified with PCR primers designed to add appropriate leader sequences to each strand and to increase restriction sites that enable cloning into the existing recombinant antibody expression vector pHB-Fc. The pHB-Fc plasmid vector was prepared as follows: the pcDNA/HA-FLAG (Accession #: FJ524378) vector was used as the starting plasmid, the constant region sequence of human IgG1 or k was added after the endonuclease EcoRI, human cytomegalovirus (HCMV) promoter sequence (Accession #: X17403) was added in front of the endonuclease HindIII, and the Chinese hamster glutamine synthetase gene (Accession #: X03495) was added after the ampicillin resistance gene and in front of the HCMV promoter.

The host cell used for protein expression is CHO-K1 cell (Cat #CCL-61) purchased from ATCC. The cells were domesticated to a CHO-K1 cell that could be suspension cultured in serum-free medium (EX-CELLTM 302) after a series of domestication steps. Using the cells, the constructed light chain and heavy chain recombinant expression plasmids were transferred into cells by electroporation. The cells were placed in an incubator for 3-5 days. The antibody concentration from the CHO-K1 transfection supernatant was measured by indirect ELISA. It showed that transfected CHO-K1 cells secreted approximately 30 mg/L of chimeric antibody.

Novartis humanized anti-IL-17 antibody (Novartis mAb) as a positive control was cloned according to the humanized sequence provided in U.S. Pat. No. 7,807,155 B2 (AIN 457) and transiently transfected for expression.

3.2 Determination of Chimeric Antibodies

Experiment Material:

Recombinant Human IL-17A, Sino Biological, 12047-HNAS

Recombinant Mouse IL-17A, Sino Biological, PBV10159R-010

Experiment Method:

The method was the same as that in Examples 1. The hybridoma supernatant was replaced with a chimeric antibody, the HRP-conjugated goat anti-mouse IgG Fc was replaced with HRP-conjugated rabbit anti-human IgG Fc antibody (Luoyang Qiongtong Experimental Material Center), and the binding activities to recombinant human and murine IL-17A were measured, respectively.

Experiment Results:

TABLE 3

Comparison of the binding activity of chimeric antibody to human IL-17A

| Sample | EC$_{50}$ (ng/ml) |
|---|---|
| positive control (Novartis mAb) | 34.1 |
| negative control (PBS) | — |
| Chimeric antibody | 38.55 |

TABLE 4

Comparison of the binging activity of chimeric antibody to mouse IL-17A

| Sample | EC$_{50}$ (ng/ml) |
|---|---|
| positive control (Novartis mAb) | — |
| negative control (PBS) | — |
| Chimeric antibody | 39.2 |

The results demonstrated that the chimeric antibody can bind to human IL-17A and can also bind to murine IL-17A with calculated EC$_{50}$ values below 40 ng/ml.

EXAMPLES 4

Preparation of Humanized Antibodies 4.1 Preparation of Humanized Antibodies

The humanization of antibodies was carried out by the following method. Briefly, the variable chain sequences of antibodies were compared to the available sequences in the NCBI protein database, and the human framework on which the CDR-grafted heavy and light chains are suitably constructed was finally determined by identification and analysis.

Based on subsequent testing and screening, one preferred FR region is the humanized FR region derived from hu-VH (SEQ ID NO: 3) and the light chain hu-VL (SEQ ID NO: 4):

hu-VH
SEQ ID NO: 3
QVQLVQSGSELKKPGASVKVSCKASGYTFTSYAMNWVRQAPGQGLEWM

GWINTNTGNPTYAQGFTGRFVFSLDTSVSTAYLQICSLKAEDTAVYYC

AR hu-VL
SEQ ID NO: 4
DIVMTQTPLSLSVTPGQPASISCKSSQSLLHSDGKTYLYWYLQKPGQP

PQLLIYEVSNRFSGVPDRFSGSGSGTDFTLKISRVEAEDVGVYYCMQS

IQLP

During the modification, the transformation site was designed according to the amino acid residues conserved in the FR region of the human antibody and the important amino acid residues in the FR region of the antibody, and the variable region of the heavy and light chain of the chimeric antibody was separately designed for humanization mutation. The expression plasmid for humanized site mutant antibody was amplified and constructed by PCR. The expression plasmid for humanized site mutant antibody was separately expressed by CHO-K1 (ATCC, NO. CCL-61) cells and purified to obtain a humanized antibody protein. A humanized antibody (named "HB0017 antibody") with excellent performance was obtained by ELISA, receptor binding inhibition assay, Biacore and cell activity assay.

The VH and VL sequences of HBH17 antibody were as shown in SEQ ID NO.: 5 and 6, respectively:

IL17-HC1-2G7
SEQ ID NO: 5
QVQLVQSGSELKKPGASVKVSCKAS<u>EYIFTNY</u>GMNWVKQAPGQGFEWM

GW<u>IDTNTGEP</u>TYAQGFTGRFVFSLDTSVSTAYLQISSLKAEDTATYYC

<u>ANYGWGYFDY</u>WGQGTTVTVSS

IL17-LC1-1C2
SEQ ID NO: 6
DVVMTQTPPSLPVNPGEPASISCRSS<u>QSLVHSNGYTY</u>LHWYLQKPGQS

PQLLIY<u>KVS</u>NHLSGVPDRFSGSGSGTDFTLKISWVEAEDVGVYFC<u>SQS</u>

<u>THVPYT</u>FGGGTKLEIK

Experimental results indicated that the humanized antibody HB0017 had better affinity and specificity compared with the murine antibody, see example 4.2.

4.2 Determination of Humanized Antibodies

Experiment Material:

Recombinant Human IL-17A, Sino Biological, 12047-HNAS

Experiment Method:

The method was the same as that in Examples 1. The hybridoma supernatant was replaced with the HB0017 antibody, the HRP-conjugated goat anti-mouse IgG Fc was replaced with HRP-conjugated rabbit anti-human IgG Fc antibody (Luoyang Qiongtong Experimental Material Center), and the binding activity to recombinant human IL-17A was measured.

Experiment Results:

TABLE 5

Comparison of the binding activity of HB0017 antibody to human IL-17A

| Sample | EC$_{50}$ (ng/ml) |
|---|---|
| positive control (Novartis mAb) | 32.9 |
| negative control (PBS) | — |
| HB0017 antibody | 15.4 |

As a result, it was confirmed that the present inventors unexpectedly obtained the humanized antibody HB0017, the human IL-17A binding activity of which was not significantly reduced, but further improved by humanization. The EC$_{50}$ was increased by about 150% (38.55/15.4−100%=150%) compared with the chimeric antibody and was increased by about 11.6 times compared with the original murine antibody. The antibody of the present invention had a lower EC$_{50}$ value and a stronger binding activity to human IL-17A than that of the positive control antibody.

EXAMPLES 5

Immune Cross-Reaction of Different Species of Humanized Monoclonal Antibodies

In this example, the antigen-antibody binding ability of the anti-IL-17A antibody to IL-17A of different species was determined by ELSIA method.

Experiment Material:
Recombinant Human IL-17A, Sino Biological, 12047-HNAS
Recombinant Rhesus IL-17A, Sino Biological, 90306-KNAB
Recombinant Mouse IL-17A, Sino Biological, PBV10159R-010
Recombinant rat IL-17A, ABGENT, PBV10154r
Experiment Method:
The method was the same as that in Examples 1. The hybridoma supernatant was replaced with the HB0017 antibody, and the HRP-conjugated goat anti-mouse IgG Fc was replaced with HRP-conjugated rabbit anti-human IgG Fc antibody (Luoyang Qiongtong Experimental Material Center), and the binding activities to human IL-17A, macaque IL-17A, mouse IL-17A and rat IL-17A were measured, respectively.
Experiment Results:

TABLE 6

Binding of HB0017 antibody to mouse IL-17A

| Sample | $EC_{50}$ (ng/ml) |
| --- | --- |
| Negative Control (PBS) | — |
| HB0017 antibody | 75.0 |

TABLE 7

Binding of HB0017 antibody to Rhesus IL-17A

| Sample | $EC_{50}$ (ng/ml) |
| --- | --- |
| Negative Control (PBS) | — |
| HB0017 antibody | 88.0 |

TABLE 8

Binding of HB0017 antibody to human IL-17A

| Sample | $EC_{50}$ (ng/ml) |
| --- | --- |
| Negative Control (PBS) | — |
| HB0017 antibody | 15.4 |

TABLE 9

Binding of HB0017 antibody to rat IL-17A

| Sample | $EC_{50}$ (ng/ml) |
| --- | --- |
| Negative Control (PBS) | — |
| HB0017 antibody | 240 |

It can be seen from Tables 6-9, in addition to binding to human IL-17A, the humanized monoclonal antibody HB0017 antibody of the present invention also bound to mouse, Rhesus and rat IL-17A, facilitating clinical animal experiments.

EXAMPLES 6

Affinity Detection of Humanized Monoclonal Antibodies

In this example, the antigen-antibody binding kinetics and affinity were determined using BIACORE method.

Experiment Material:
Recombinant human IL-17A, Sino Biological, 12047-HNAS
Amine Coupling Kit, GE, BR-1000-50
HBS-EP (10×), GE, BR-1006-69
Human Antibody Captrue Kit, GE, BR-1008-39
Experiment Method:
Human Antibody Capture Antiboy was amino-coupled immobilized on the Sereis S Sensor Chip CM5 chip using Amine Coupling Kit, anti-Human Capture-CM5 chip. The chip was placed at room temperature for 20-30 mins, and loaded into the instrument. The antigen was diluted with equilibration buffer at an initial dilution of 10 nM, and was diluted for 5 concentration gradients. 2 zero concentrations (i.e., equilibration buffer) and one repeat concentration (generally the lowest concentration repeat) were set. The antibody sample was diluted to the experimental working concentration with an equilibration buffer and sealed at 2-8° C. After the sample analysis was completed, the corresponding analysis program was used to analyze the data, confirming that there was no obvious reference binding and the kinetics, 1:1 binding model was selected for fitting the analysis results to obtain the kinetic parameters of the sample.
Experiment Results:

TABLE 10

Affinity test results of HB0017 antibody to human IL-17a

| Sample | Ka (1/Ms) | Kd(1/s) | KD(M) |
| --- | --- | --- | --- |
| positive control (Novartis mAb) | 1.46E+06 | 1.61E−04 | 1.11E−10 |
| HB0017 | 4.55E+06 | 9.02E−05 | 1.98E−11 |

The affinity constant (KD(M)) to human IL-17A showed that the HB0017 antibody of the present invention has a stronger affinity that is nearly an order of magnitude higher than that of the positive control antibody.

EXAMPLES 7

Determination of Biological Activity of Humanized Monoclonal Antibodies at Cellular Level IL-17A can stimulate HT1080 to produce IL-6 under the synergistic effect of TNFα or TNFβ. The neutralizing effect of IL-17A by the HB0017 antibody further inhibited the expression level of IL-6. The biological activity of the antibodies of the invention was demonstrated.
Experiment Material:
DMEM Glutamine+10% Inactivated fetal bovine serum (FBS)+1% PS (double antibody) (growth medium)
Recombinant human IL-17A, Sino Biological, 12047-HNAS
Recombinant human TNFα, Sino Biological, 10602-HNAE
Human IL-6 ELISA MAX™ Deluxe Set, 430506, BioLegend
Experiment Method:
HT1080 cells in logarithmic growth phase were taken, and the experiment can be carried out at the confluence of 80% to 90%. The culture medium in the cell culture flask was discarded, and the flask was washed once with PBS. Appropriate amount of 0.25% pancreatin and ~0.02% EDTA digestion solution were added and put into the cell incubator. After 1-2 min, the culture flask was tapped to cause the cells to fall off. The growth medium was added to prepare a single cell suspension, and the cells were centrifuged at 1000 rpm for 5 min. The cells were resuspended in growth medium and counted. The cells were diluted to $2.5 \times 10^5$/ml with growth medium, and was added to the cell culture plate at 50 μl/well, and then cultured in a cell culture incubator for 5 hours or longer to adhere the cells. The antibody and the positive control were diluted to 200 μg/ml with blank medium (DMEM glutamine) at an initial dilution of 200 μg/ml, and was diluted by 3.16 folds for eight gradient concentrations. The recombinant human IL-17A was diluted to 40 ng/ml with blank medium, and the recombinant human TNF-α was diluted to 20 ng/ml with blank medium. The diluted recombinant human IL-17A and recombinant human TNF-α were mixed at a volume ratio of 1:1. Then, it was mixed the antibody or the positive control of 9 gradient concentrations at a volume ratio of 1:1, and incubated at 37° C. for 1 hour.

50 μl/well of each incubated antibody or positive control of 9 gradient concentrations was added to the 96-well cell culture plate, duplicate for each concentration. 50 μl of IL-17 & TNFα mixture was used in positive control wells and 50 μl of blank medium was used in blank control wells, respectively in triplicate. The cell culture plates were then cultured overnight at 37° C. under 5% $CO_2$.

The ELISA plate was coated according to Human IL-6 ELISA MAXTM Deluxe Set Kit, and the 96-well cell culture plate cultured overnight was taken out on the next day, and the culture supernatant was drawn and diluted at 20×. ELISA was performed according to Human IL-6 ELISA MAXTM Deluxe Set instructions.

Experiment Results:

TABLE 11

Results of HB0017 antibody biological activity assay

| Sample | $IC_{50}$ (μg/ml) | $IC_{80}$ (μg/ml) | $IC_{90}$ (μg/ml) |
|---|---|---|---|
| Positive control (Novartis mAb) | 0.52 | 2.11 | 4.80 |
| HB0017 antibody | 0.09 | 0.13 | 0.17 |

The results in Table 11 showd that the biological activity of the HB0017 antibody of the present invention was increased by nearly 6-fold as compared with the positive control antibody, and the HB0017 antibody had good biological activity.

EXAMPLES 8

Antigen Binding Specificity of Humanized Monoclonal Antibodies

In this example, the binding specificity of the HB0017 antibody to different subtypes of IL-17 was tested.

Experiment Material:
Recombinant Human IL-17A, Sino Biological, 12047-HNAS
Recombinant human IL-17B, R&D, 8129-IL
Recombinant human IL-17D, Sino Biologica, 10076-H08S
Recombinant human IL-17E, ABGENT, PBV10154r
Recombinant human IL-17F, Sino Biological, 11855-H07H-5
Recombinant human IL-17A/F, Sino Biological, CT047-H08H-20

Experiment Method:
The method was the same as that in Examples 1. The hybridoma supernatant was replaced with the HB0017 antibody, and the HRP-conjugated goat anti-mouse IgG Fc was replaced with HRP-conjugated rabbit anti-human IgG Fc antibody (Luoyang Qiongtong Experimental Material Center), and the binding activities to human IL-17A, human IL-17B, human IL-17C, human IL-17D, human IL-17E, human IL-17F and human IL-17A/F were measured, respectively.

Experiment Results:

TABLE 12

Binding specificity results of HB0017 antibody to human IL-17 family

| | $EC_{50}$ ng/ml | | | | | |
|---|---|---|---|---|---|---|
| Sample | Human IL-17A | Human IL-17A/F | Human IL-17B | Human IL-17D | Human IL-17E | Human IL-17F |
| Negative Control (PBS) | — | — | — | — | — | — |
| HB0017 antibody | 15.4 | 80 | NA | NA | NA | NA |

The results in Table 12 showd that HB0017 antibody could bind to human IL-17A and IL-17A/F, and not bind to other family members IL-17B, IL-17D, IL-17E and IL-17F, and had good antigen binding specificity.

EXAMPLES 9

In Vivo Efficacy Testing of Humanized Monoclonal Antibodies

This example was carried out using the imiquimod-induced mouse psoriasis model to verify whether the symptoms or related indicators of psoriasis can be improved by the antibodies of the invention by blocking the binding of IL-17 to the IL-17 receptor (eg, hIL-17RA) in vivo.

The test method was as follows;
32 C57BL/6 female mice (about 20 g) were taken and their backs were depilated and were sensitized three days later. Two days before sensitizing, the mice were randomly divided into 4 group (8 in each group): group I was a solvent control group and was administered with PBS; group II was the isotype control group, and human IgG1 (diluted with PBS), the negative control sample was given 100 mg/kg; group III was the HB0017 antibody administration group, and the HB0017 antibody was administered at 100 mg/kg; and group IV was a positive control group, and dexamethasone (diluted with PBS) was administered at 1 mg/kg. Each of the above groups was intraperitoneally injected with the drug once on the day of grouping and on the second day of modeling (day 2). On the day of sensitization (day 1), about 62.5 mg of imiquimod cream (5%) was applied to the right ear and back skin of mice in each group for 5 consecutive days.

The thicknesses of the right ear of the mice were measured by a spiral micrometer every day from the day of sensitizing, and the thickness of the ear swelling of the mouse was calculated using the thickness of the right ear at day 0 as a control. At the same time, the mice were weighed daily, and the skin scales, induration and erythema were observed and scored. A 4-level scoring method was used: 0 points, no disease; 1 point, slight; 2 points, moderate; 3 points, severe; 4 points, very serious.

The results were shown in FIG. 1. The results indicated that the humanized anti-IL-17A antibody HB0017 of the present invention has a significant improvement effect on the imiquimod-induced mouse psoriasis model compared with dexamethasone.

All literatures mentioned in the present application are incorporated herein by reference, as though each one is individually incorporated by reference. Additionally, it should be understood that after reading the above teachings, those skilled in the art can make various changes and modifications to the present invention. These equivalents also fall within the scope defined by the appended claims.

The invention claimed is:

1. A heavy chain variable region of an antibody, wherein the heavy chain variable region comprise three complementary determining regions CDR:
   CDR1 as shown in SEQ ID NO: 7,
   CDR2 as shown in SEQ ID NO: 8 and
   CDR3 as shown in SEQ ID NO: 9.

2. The heavy chain variable region according to claim 1, wherein the heavy chain variable region has the amino acid sequence as shown in SEQ ID NO: 1 or 5.

3. An antibody having:
   (i) the heavy chain variable region of claim 1; and
   (ii) a light chain variable region, wherein the light chain variable region comprises three complementary determining regions CDR:
   CDR1' as shown in SEQ ID NO: 10,
   CDR2' with the amino acid sequence of KVS, and
   CDR3' as shown in SEQ ID NO: 11.

4. The antibody according to claim 3, wherein the antibody is selected from an animal-derived antibody, a chimeric antibody, a humanized antibody, or a combination thereof.

5. The antibody according to claim 3, wherein the heavy chain variable region sequence of the antibody is as shown in SEQ ID NO: 1 or 5; and/or
   the light chain variable region sequence of the antibody is as shown in SEQ ID NO: 2 or 6.

6. A pharmaceutical composition, which comprises:
   (i) an active ingredient which is the antibody of claim 3; and
   (ii) a pharmaceutically acceptable carrier.

7. A method of treating a disease related to IL-17A, which comprises: administering the antibody of claim 3 to a subject in need thereof.

8. The method of claim 7, wherein the disease related to IL-17A is selected from inflammation, autoimmune disease, or a combination thereof.

9. The method of claim 7, wherein the disease related to IL-17A is selected from psoriasis, psoriatic arthritis, ankylosing spondylitis, multiple sclerosis, inflammatory arthritis, or a combination thereof.

10. The method of claim 9, wherein the inflammatory arthritis is selected from osteoarthritis, rheumatoid arthritis, rheumatic arthritis, or a combination thereof.

11. The antibody according to claim 3, wherein the heavy chain variable region sequence of the antibody is as shown in SEQ ID NO: 1; and the light chain variable region sequence of the antibody is as shown in SEQ ID NO: 2.

12. The antibody according to claim 3, wherein the heavy chain variable region sequence of the antibody is as shown in SEQ ID NO: 5; and the light chain variable region sequence of the antibody is as shown in SEQ ID NO: 6.

13. The antibody according to claim 3, wherein the antibody is in the form of a drug conjugate.

14. The antibody according to claim 3, wherein the antibody further comprises a coupling moiety coupled to the antibody, the coupling moiety being selected from a detectable label, a drug, a toxin, a cytokine, a radionuclide, an enzyme, or a combination thereof.

15. A recombinant protein having:
   (i) the heavy chain variable region of claim 1; and
   (ii) optionally a tag sequence that assists in expression and/or purification.

16. A chimeric antigen receptor (CAR) construct, wherein the scFV segment of the monoclonal antibody antigen binding region of the CAR construct is a binding region that specifically binds to IL-17A, and the scFv has the heavy chain variable region of claim 1 and a light chain variable region, wherein the light chain variable region comprises three complementary determining regions CDR:
   CDR1' as shown in SEQ ID NO: 10,
   CDR2' with the amino acid sequence of KVS, and
   CDR3' as shown in SEQ ID NO: 11.

* * * * *